(12) United States Patent
Francischelli

(10) Patent No.: US 8,262,649 B2
(45) Date of Patent: *Sep. 11, 2012

(54) METHOD AND APPARATUS FOR TISSUE ABLATION

(75) Inventor: David E. Francischelli, Anoka, MN (US)

(73) Assignee: Medtronic, Inc., Minneapolis, MN (US)

( * ) Notice: Subject to any disclaimer, the term of this patent is extended or adjusted under 35 U.S.C. 154(b) by 500 days.

This patent is subject to a terminal disclaimer.

(21) Appl. No.: 11/881,422

(22) Filed: Jul. 27, 2007

(65) Prior Publication Data

US 2007/0270799 A1    Nov. 22, 2007

Related U.S. Application Data

(63) Continuation of application No. 11/411,261, filed on Apr. 26, 2006, now Pat. No. 7,250,051, which is a continuation of application No. 10/756,437, filed on Jan. 13, 2004, now Pat. No. 7,094,235, which is a continuation of application No. 10/016,297, filed on Dec. 12, 2001, now Pat. No. 6,699,240.

(60) Provisional application No. 60/286,953, filed on Apr. 26, 2001.

(51) Int. Cl.
*A61B 18/02* (2006.01)

(52) U.S. Cl. ............... 606/23; 606/20; 606/22; 606/24; 606/26; 606/52; 607/96; 607/98; 607/102

(58) Field of Classification Search ............... 606/41, 606/49–51; 607/99, 129
See application file for complete search history.

(56) References Cited

U.S. PATENT DOCUMENTS

| | | |
|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |

(Continued)

FOREIGN PATENT DOCUMENTS

WO    WO 99/12488    3/1999

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner* — Aaron Roane

(57) ABSTRACT

A method for ablation in which a portion of atrial tissue around the pulmonary veins of the heart is ablated by a first elongated ablation component and a second elongated ablation component movable relative to the first ablation component and having means for magnetically attracting the first and second components toward one another. The magnetic means draw the first and second components toward one another to compress the atrial tissue therebetween, along the length of the first and second components and thereby position the device for ablation of the tissue.

6 Claims, 6 Drawing Sheets

U.S. PATENT DOCUMENTS

| | | | |
|---|---|---|---|
| 3,907,339 A | 9/1975 | Stumpf et al. | |
| 3,910,277 A | 10/1975 | Zimmer | |
| 3,913,581 A | 10/1975 | Ritson et al. | |
| 3,924,628 A | 12/1975 | Droegemueller et al. | |
| 3,924,631 A | 12/1975 | Mancusi, Jr. | |
| 4,018,227 A | 4/1977 | Wallach | |
| 4,022,215 A | 5/1977 | Benson | |
| 4,061,135 A | 12/1977 | Widran et al. | |
| 4,063,560 A | 12/1977 | Thomas et al. | |
| 4,072,152 A | 2/1978 | Linehan | |
| 4,082,096 A | 4/1978 | Benson | |
| 4,207,897 A | 6/1980 | Lloyd et al. | |
| 4,248,224 A | 2/1981 | Jones | |
| 4,275,734 A | 6/1981 | Mitchiner | |
| 4,278,090 A | 7/1981 | van Gerven | |
| 4,377,168 A | 3/1983 | Rzasa et al. | |
| 4,519,389 A | 5/1985 | Gudkin et al. | |
| 4,598,698 A | 7/1986 | Siegmund | |
| 4,601,290 A | 7/1986 | Effron et al. | |
| 4,664,110 A | 5/1987 | Schanzlin | |
| 4,736,749 A | 4/1988 | Lundback | |
| 4,779,611 A | 10/1988 | Grooters et al. | |
| 4,802,475 A | 2/1989 | Weshahy | |
| 4,815,470 A | 3/1989 | Curtis et al. | |
| 4,872,346 A | 10/1989 | Kelly-Fry et al. | |
| 4,916,922 A | 4/1990 | Mullens | |
| 4,917,095 A | 4/1990 | Fry et al. | |
| 4,936,281 A | 6/1990 | Stasz | |
| 4,946,460 A | 8/1990 | Merry et al. | |
| 5,013,312 A | 5/1991 | Parins et al. | |
| 5,029,574 A | 7/1991 | Shimamura et al. | |
| 5,044,165 A | 9/1991 | Linner et al. | |
| 5,078,713 A | 1/1992 | Varney | |
| 5,080,102 A | 1/1992 | Dory | |
| 5,080,660 A | 1/1992 | Buelna | |
| 5,100,388 A | 3/1992 | Behl et al. | |
| 5,108,390 A | 4/1992 | Potocky et al. | |
| 5,147,355 A | 9/1992 | Friedman et al. | |
| 5,178,133 A | 1/1993 | Pena | |
| 5,207,674 A | 5/1993 | Hamilton | |
| 5,217,860 A | 6/1993 | Fahy et al. | |
| 5,222,501 A | 6/1993 | Ideker et al. | |
| 5,224,943 A | 7/1993 | Goddard | |
| 5,228,923 A | 7/1993 | Hed | |
| 5,231,995 A | 8/1993 | Desai | |
| 5,232,516 A | 8/1993 | Hed | |
| 5,254,116 A | 10/1993 | Baust et al. | |
| 5,263,493 A | 11/1993 | Avitall | |
| 5,269,291 A | 12/1993 | Carter | |
| 5,275,595 A | 1/1994 | Dobak, III | |
| 5,277,201 A | 1/1994 | Stern | |
| 5,281,213 A | 1/1994 | Milder et al. | |
| 5,281,215 A | 1/1994 | Milder | |
| 5,295,484 A | 3/1994 | Marcus et al. | |
| 5,309,896 A | 5/1994 | Moll et al. | |
| 5,316,000 A | 5/1994 | Chapelon et al. | |
| 5,317,878 A | 6/1994 | Bradshaw et al. | |
| 5,318,525 A | 6/1994 | West et al. | |
| 5,322,520 A | 6/1994 | Milder | |
| 5,323,781 A | 6/1994 | Ideker et al. | |
| 5,324,255 A | 6/1994 | Passafaro et al. | |
| 5,324,284 A | 6/1994 | Imran | |
| 5,324,286 A | 6/1994 | Fowle et al. | |
| 5,334,181 A | 8/1994 | Rubinsky et al. | |
| 5,334,193 A | 8/1994 | Nardella | |
| 5,348,554 A | 9/1994 | Imran et al. | |
| 5,353,783 A | 10/1994 | Nakao et al. | |
| 5,354,258 A | 10/1994 | Dory | |
| 5,357,956 A | 10/1994 | Nardella | 128/642 |
| 5,361,752 A | 11/1994 | Moll et al. | |
| 5,385,148 A | 1/1995 | Lesh et al. | |
| 5,396,887 A | 3/1995 | Imran | |
| 5,397,304 A | 3/1995 | Truckai | |
| 5,400,770 A | 3/1995 | Nakao et al. | |
| 5,400,783 A | 3/1995 | Pomeranz et al. | |
| 5,403,309 A | 4/1995 | Coleman et al. | |
| 5,403,311 A | 4/1995 | Abele et al. | |
| 5,405,376 A | 4/1995 | Mulier et al. | |
| 5,409,483 A | 4/1995 | Campbell et al. | |
| 5,423,807 A | 6/1995 | Milder | |
| 5,423,811 A | 6/1995 | Imran et al. | |
| 5,427,119 A | 6/1995 | Swartz et al. | |
| 5,429,131 A | 7/1995 | Scheinman et al. | 600/374 |
| 5,431,649 A | 7/1995 | Mulier et al. | |
| 5,433,708 A | 7/1995 | Nichols et al. | |
| 5,435,308 A | 7/1995 | Gallup et al. | |
| 5,437,651 A | 8/1995 | Todd et al. | |
| 5,443,463 A | 8/1995 | Stern et al. | |
| 5,443,470 A | 8/1995 | Stern et al. | |
| 5,450,843 A | 9/1995 | Moll et al. | |
| 5,452,582 A | 9/1995 | Longsworth | |
| 5,452,733 A | 9/1995 | Sterman et al. | |
| 5,462,545 A | 10/1995 | Wang et al. | |
| 5,465,717 A | 11/1995 | Imran et al. | |
| 5,469,853 A | 11/1995 | Law et al. | |
| 5,472,876 A | 12/1995 | Fahy | |
| 5,478,309 A | 12/1995 | Sweezer et al. | |
| 5,478,330 A | 12/1995 | Imran et al. | |
| 5,486,193 A | 1/1996 | Bourne et al. | |
| 5,487,385 A | 1/1996 | Avitall | |
| 5,487,757 A | 1/1996 | Truckai et al. | |
| 5,496,312 A | 3/1996 | Klicek | |
| 5,497,774 A | 3/1996 | Swartz et al. | |
| 5,498,248 A | 3/1996 | Milder | |
| 5,500,012 A | 3/1996 | Brucker et al. | |
| 5,505,730 A | 4/1996 | Edwards | |
| 5,516,505 A | 5/1996 | McDow | |
| 5,520,682 A | 5/1996 | Baust et al. | |
| 5,522,870 A | 6/1996 | Ben-Zion | |
| 5,536,267 A | 7/1996 | Edwards et al. | |
| 5,545,195 A | 8/1996 | Lennox et al. | |
| 5,545,200 A | 8/1996 | West et al. | |
| 5,549,661 A | 8/1996 | Kordis et al. | |
| 5,555,883 A | 9/1996 | Avitall | |
| 5,560,362 A | 10/1996 | Sliwa, Jr. et al. | |
| 5,562,720 A | 10/1996 | Stern et al. | |
| 5,569,241 A | 10/1996 | Edwards | |
| 5,571,088 A | 11/1996 | Lennox et al. | |
| 5,571,215 A | 11/1996 | Sterman et al. | |
| 5,573,532 A | 11/1996 | Chang et al. | |
| 5,575,766 A | 11/1996 | Swartz et al. | 604/53 |
| 5,575,788 A | 11/1996 | Baker et al. | |
| 5,575,810 A | 11/1996 | Swanson et al. | |
| 5,578,007 A | 11/1996 | Imran | |
| 5,582,609 A | 12/1996 | Swanson et al. | |
| 5,588,432 A | 12/1996 | Crowley | |
| 5,590,657 A | 1/1997 | Cain et al. | |
| 5,595,183 A | 1/1997 | Swanson et al. | |
| 5,596,995 A | 1/1997 | Sherman et al. | 128/736 |
| 5,607,462 A | 3/1997 | Imran | |
| 5,617,854 A | 4/1997 | Munsif | |
| 5,630,837 A | 5/1997 | Crowley | |
| 5,637,090 A | 6/1997 | McGee et al. | |
| 5,643,197 A | 7/1997 | Brucker et al. | |
| 5,656,029 A | 8/1997 | Imran et al. | |
| 5,658,278 A | 8/1997 | Imran et al. | |
| 5,671,747 A | 9/1997 | Connor | |
| 5,673,695 A | 10/1997 | McGee et al. | |
| 5,676,662 A | 10/1997 | Fleischhacker et al. | |
| 5,676,692 A | 10/1997 | Sanghvi et al. | |
| 5,676,693 A | 10/1997 | Lafontaine | |
| 5,678,550 A | 10/1997 | Bassen et al. | |
| 5,680,860 A | 10/1997 | Imran | |
| 5,681,278 A | 10/1997 | Igo et al. | |
| 5,681,308 A | 10/1997 | Edwards et al. | |
| 5,685,878 A | 11/1997 | Falwell et al. | 606/49 |
| 5,687,723 A | 11/1997 | Avitall | |
| 5,687,737 A | 11/1997 | Branham et al. | |
| 5,688,267 A | 11/1997 | Panescu et al. | 606/41 |
| RE4,794 E | 12/1997 | Eggers et al. | |
| 5,697,536 A | 12/1997 | Eggers et al. | |
| 5,697,882 A | 12/1997 | Eggers et al. | |
| 5,697,925 A | 12/1997 | Taylor | |
| 5,697,927 A | 12/1997 | Imran et al. | |
| 5,697,928 A | 12/1997 | Walcott et al. | |
| 5,713,942 A | 2/1998 | Stern | |
| 5,716,389 A | 2/1998 | Walinsky et al. | |

| Patent No. | Date | Inventor | Class |
|---|---|---|---|
| 5,718,241 A | 2/1998 | Ben-Haim et al. | |
| 5,718,701 A | 2/1998 | Shai et al. | 606/41 |
| 5,720,775 A | 2/1998 | Lanard | |
| 5,722,402 A | 3/1998 | Swanson et al. | |
| 5,730,074 A | 3/1998 | Peter | |
| 5,730,127 A | 3/1998 | Avitall | |
| 5,730,704 A | 3/1998 | Avitall | |
| 5,733,280 A | 3/1998 | Avitall | 606/23 |
| 5,735,280 A | 4/1998 | Sherman et al. | |
| 5,735,290 A | 4/1998 | Sterman et al. | |
| 5,755,760 A | 5/1998 | Maguire et al. | |
| 5,769,846 A | 6/1998 | Edwards et al. | |
| 5,782,828 A | 7/1998 | Chen et al. | |
| 5,785,706 A | 7/1998 | Bednarek | |
| 5,788,636 A | 8/1998 | Curley | |
| 5,792,140 A | 8/1998 | Tu et al. | |
| 5,797,960 A | 8/1998 | Stevens et al. | |
| 5,800,428 A | 9/1998 | Nelson et al. | |
| 5,800,482 A | 9/1998 | Pomeranz et al. | |
| 5,810,802 A | 9/1998 | Panescu et al. | |
| 5,827,216 A | 10/1998 | Igo et al. | |
| 5,836,947 A | 11/1998 | Fleischman et al. | |
| 5,840,030 A | 11/1998 | Ferek-Petric et al. | |
| 5,844,349 A | 12/1998 | Oakley et al. | |
| 5,846,187 A | 12/1998 | Wells et al. | |
| 5,846,191 A | 12/1998 | Wells et al. | |
| 5,849,028 A | 12/1998 | Chen | |
| 5,871,523 A | 2/1999 | Fleischman et al. | 607/99 |
| 5,871,525 A | 2/1999 | Edwards et al. | |
| 5,873,845 A | 2/1999 | Cline et al. | |
| 5,876,399 A | 3/1999 | Chia et al. | |
| 5,879,295 A | 3/1999 | Li et al. | |
| 5,879,296 A | 3/1999 | Ockuly et al. | |
| 5,881,732 A | 3/1999 | Sung et al. | |
| 5,882,346 A | 3/1999 | Pomeranz et al. | |
| 5,885,278 A | 3/1999 | Fleischman | |
| 5,893,848 A | 4/1999 | Negus et al. | |
| 5,895,417 A | 4/1999 | Pomeranz et al. | 607/101 |
| 5,897,553 A | 4/1999 | Mulier | |
| 5,897,554 A | 4/1999 | Chia et al. | |
| 5,899,898 A | 5/1999 | Arless et al. | |
| 5,899,899 A | 5/1999 | Arless et al. | |
| 5,902,289 A | 5/1999 | Swartz et al. | |
| 5,904,711 A | 5/1999 | Flom et al. | |
| 5,906,580 A | 5/1999 | Kline-Schoder et al. | |
| 5,906,587 A | 5/1999 | Zimmon | |
| 5,906,606 A | 5/1999 | Chee et al. | |
| 5,908,029 A | 6/1999 | Knudson et al. | |
| 5,916,214 A | 6/1999 | Cosio et al. | |
| 5,921,924 A | 7/1999 | Avitall | |
| 5,921,982 A | 7/1999 | Lesh et al. | |
| 5,927,284 A | 7/1999 | Borst et al. | |
| 5,928,191 A | 7/1999 | Houser et al. | |
| 5,931,810 A | 8/1999 | Grabek | |
| 5,931,848 A | 8/1999 | Saadat | |
| 5,954,661 A | 9/1999 | Greenspon et al. | |
| 5,971,980 A | 10/1999 | Sherman | |
| 5,971,983 A | 10/1999 | Lesh | |
| 5,993,447 A | 11/1999 | Blewett et al. | |
| 6,007,499 A | 12/1999 | Martin et al. | |
| 6,012,457 A | 1/2000 | Lesh | |
| 6,016,811 A | 1/2000 | Knopp et al. | |
| 6,032,077 A | 2/2000 | Pomeranz | 607/101 |
| 6,042,556 A | 3/2000 | Beach et al. | |
| 6,045,550 A | 4/2000 | Simpson et al. | 606/42 |
| 6,056,743 A | 5/2000 | Ellis et al. | 606/15 |
| 6,063,081 A | 5/2000 | Mulier | |
| 6,068,629 A * | 5/2000 | Haissaguerre et al. | 606/41 |
| 6,071,279 A | 6/2000 | Whayne et al. | |
| 6,088,894 A | 7/2000 | Oakley | |
| 6,096,037 A | 8/2000 | Mulier et al. | 606/49 |
| 6,113,592 A | 9/2000 | Taylor | |
| 6,117,101 A | 9/2000 | Diederich et al. | |
| 6,120,496 A | 9/2000 | Whayne et al. | |
| 6,133,592 A | 10/2000 | Kishimoto et al. | 257/190 |
| 6,142,944 A | 11/2000 | Li et al. | 600/453 |
| 6,142,993 A | 11/2000 | Whayne et al. | |
| 6,142,994 A | 11/2000 | Swanson et al. | |
| 6,152,920 A | 11/2000 | Thompson et al. | |
| 6,161,543 A | 12/2000 | Cox et al. | 128/898 |
| 6,165,174 A | 12/2000 | Jacobs et al. | |
| 6,217,528 B1 | 4/2001 | Koblish et al. | |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,235,024 B1 | 5/2001 | Tu | |
| 6,237,605 B1 | 5/2001 | Vaska et al. | 128/898 |
| 6,238,347 B1 | 5/2001 | Nix et al. | |
| 6,238,393 B1 | 5/2001 | Mulier | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,251,092 B1 | 6/2001 | Qin et al. | |
| 6,251,128 B1 | 6/2001 | Knopp et al. | |
| 6,270,471 B1 | 8/2001 | Hechel et al. | |
| 6,293,943 B1 | 9/2001 | Panescu et al. | |
| 6,296,619 B1 | 10/2001 | Brisken et al. | |
| 6,302,880 B1 | 10/2001 | Schaer | |
| 6,311,692 B1 | 11/2001 | Vaska et al. | |
| 6,312,383 B1 | 11/2001 | Lizzi et al. | |
| 6,314,962 B1 | 11/2001 | Vaska et al. | |
| 6,314,963 B1 | 11/2001 | Vaska et al. | |
| 6,325,797 B1 | 12/2001 | Stewart et al. | |
| 6,328,736 B1 | 12/2001 | Mulier | |
| 6,332,881 B1 | 12/2001 | Carner et al. | |
| 6,358,248 B1 | 3/2002 | Mulier | |
| 6,361,531 B1 | 3/2002 | Hissong | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,383,151 B1 | 5/2002 | Diederich et al. | |
| 6,385,472 B1 | 5/2002 | Hall et al. | |
| 6,398,792 B1 | 6/2002 | O'Connor | |
| 6,409,722 B1 | 6/2002 | Hoey | |
| 6,413,254 B1 | 7/2002 | Hissong et al. | |
| 6,419,648 B1 | 7/2002 | Vitek et al. | |
| 6,425,867 B1 | 7/2002 | Vaezy et al. | |
| 6,430,426 B2 | 8/2002 | Avitall | |
| 6,440,130 B1 | 8/2002 | Mulier | |
| 6,443,952 B1 | 9/2002 | Mulier | |
| 6,447,507 B1 | 9/2002 | Bednarek et al. | |
| 6,461,314 B1 | 10/2002 | Pant et al. | |
| 6,461,356 B1 | 10/2002 | Patterson | |
| 6,464,700 B1 | 10/2002 | Koblish et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,216 B2 | 11/2002 | Mulier | |
| 6,484,727 B1 * | 11/2002 | Vaska et al. | 128/898 |
| 6,488,680 B1 | 12/2002 | Francischelli | |
| 6,502,575 B1 | 1/2003 | Jacobs et al. | |
| 6,514,250 B1 | 2/2003 | Jahns | |
| 6,527,767 B2 | 3/2003 | Wang et al. | |
| 6,537,248 B2 | 3/2003 | Mulier | |
| 6,537,272 B2 | 3/2003 | Christopherson et al. | |
| 6,546,935 B2 * | 4/2003 | Hooven | 128/898 |
| 6,558,382 B2 | 5/2003 | Jahns | |
| 6,584,360 B2 | 6/2003 | Francischelli | |
| 6,585,732 B2 | 7/2003 | Mulier | |
| 6,605,084 B2 | 8/2003 | Acker et al. | |
| 6,610,055 B1 | 8/2003 | Swanson et al. | |
| 6,610,060 B2 | 8/2003 | Mulier | |
| 6,613,048 B2 | 9/2003 | Mulier | |
| 6,645,199 B1 | 11/2003 | Jenkins et al. | |
| 6,656,175 B2 | 12/2003 | Francischelli | |
| 6,692,450 B1 | 2/2004 | Coleman | |
| 6,699,240 B2 | 3/2004 | Francischelli | |
| 6,702,811 B2 | 3/2004 | Stewart et al. | |
| 6,706,038 B2 | 3/2004 | Francischelli | |
| 6,706,039 B2 | 3/2004 | Mulier | |
| 6,716,211 B2 | 4/2004 | Mulier | |
| 6,736,810 B2 | 5/2004 | Hoey | |
| 6,755,827 B2 | 6/2004 | Mulier | |
| 6,764,487 B2 | 7/2004 | Mulier | |
| 6,773,433 B2 | 8/2004 | Stewart et al. | |
| 6,776,780 B2 | 8/2004 | Mulier | |
| 6,807,968 B2 | 10/2004 | Francischelli | |
| 6,827,715 B2 | 12/2004 | Francischelli | |

| | | | |
|---|---|---|---|
| 6,849,073 B2 | 2/2005 | Hoey | |
| 6,858,028 B2 | 2/2005 | Mulier | |
| 6,887,238 B2 | 5/2005 | Jahns | |
| 6,899,711 B2 | 5/2005 | Stewart et al. | |
| 6,911,019 B2 | 6/2005 | Mulier | |
| 6,916,318 B2 | 7/2005 | Francischelli | |
| 6,936,046 B2 | 8/2005 | Hissong | |
| 6,949,097 B2 | 9/2005 | Stewart et al. | |
| 6,949,098 B2 | 9/2005 | Mulier | |
| 6,960,205 B2 | 11/2005 | Jahns | |
| 6,962,589 B2 | 11/2005 | Mulier | |
| 7,094,235 B2 * | 8/2006 | Francischelli | 606/51 |
| 7,250,051 B2 * | 7/2007 | Francischelli | 606/51 |
| 2003/0045872 A1 | 3/2003 | Jacobs | |
| 2003/0144656 A1 | 7/2003 | Ocel | |
| 2003/0191462 A1 | 10/2003 | Jacobs | |
| 2003/0216724 A1 | 11/2003 | Jahns | |
| 2004/0015106 A1 | 1/2004 | Coleman | |
| 2004/0015219 A1 | 1/2004 | Francischelli | |
| 2004/0044340 A1 | 3/2004 | Francischelli | |
| 2004/0049179 A1 | 3/2004 | Francischelli | |
| 2004/0078069 A1 | 4/2004 | Francischelli | |
| 2004/0082948 A1 | 4/2004 | Stewart et al. | |
| 2004/0087940 A1 | 5/2004 | Jahns | |
| 2004/0092926 A1 | 5/2004 | Hoey | |
| 2004/0138621 A1 | 7/2004 | Jahns | |
| 2004/0138656 A1 | 7/2004 | Francischelli | |
| 2004/0143260 A1 | 7/2004 | Francischelli | |
| 2004/0186465 A1 | 9/2004 | Francischelli | |
| 2004/0215183 A1 | 10/2004 | Hoey | |
| 2004/0220560 A1 | 11/2004 | Briscoe | |
| 2004/0236322 A1 | 11/2004 | Mulier | |
| 2004/0267326 A1 | 12/2004 | Ocel | |
| 2005/0010095 A1 | 1/2005 | Stewart et al. | |
| 2005/0033280 A1 | 2/2005 | Francischelli | |
| 2005/0090815 A1 | 4/2005 | Francischelli | |
| 2005/0143729 A1 | 6/2005 | Francischelli | |
| 2005/0165392 A1 | 7/2005 | Francischelli | |
| 2005/0209564 A1 | 9/2005 | Bonner | |
| 2005/0267454 A1 | 12/2005 | Hissong | |
| 2006/0009756 A1 | 1/2006 | Francischelli | |
| 2006/0009759 A1 | 1/2006 | Christian | |
| 2007/0270800 A1 | 11/2007 | Francischelli | |
| 2008/0071271 A1 | 3/2008 | Francischelli | |

FOREIGN PATENT DOCUMENTS

| | | |
|---|---|---|
| WO | WO 99/59486 | 11/1999 |
| WO | WO 01/05306 | 1/2001 |
| WO | WO 01/72234 | 10/2001 |
| WO | WO 01/80724 | 11/2001 |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.
Sealy, "Direct Surgical Treatment of Arrhythmias: The Last Frontier in Surgical Cardiology," Chest 75(5): 536-537, 1979.
Sealy, "The Evolution of the Surgical Methods for Interruption of Right Free Wall Kent Bundles," The Annals of Thoracic Surgery 36(1): 29-36, 1983.
Guiraudon et al., "Surgical Repair of Wolff-Parkinson-White Syndrome: A New Closed-Heart Techique," The Annals of Thoracic Surgery 37(1): 67-71, 1984.
Klein et al., "Surgical Correction of the Wolff-Parkinson-White Syndrome in the Closed Heart Using Cryosurgery: A Simplified Approach," JACC 3(2): 405-409, 1984.
Randall et al., "Local Epicardial Chemical Ablation of Vagal Input to Sino-Atrial and Atrioventricular Regions of the Canine Heart," Journal of the Autonomic Nervous System 11:145-159, 1984.
Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.
Gallagher et al., "Surgical Treatment of Arrhythmias," The American Journal of Cardiology 6I:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.
Cox et al., Surgery for Atrial Fibrillation; Seminars in Thoracic and Cardiovascular Surgery , vol. 1, No. 1 (Jul. 1989) pp. 67-73.
Bredikis and Bredikis; Surgery of Tachyarrhythmia: Intracardiac Closed Heart Cryoablation; PACE, vol. 13, pp. 1980-1984.
McCarthy et al., "Combined Treatment of Mitral Regurgitation and Atrial Fibrillation with Valvuloplasty and the Maze Procedure," The American Journal of Cardiology 71: 483-486, 1993.
Yamauchi et al. "Use of Intraoperative Mapping to Optimize Surgical Ablation of Atrial Flutter," The Annals of Thoracic Surgery 56: 337-342, 1993.
Graffigna et al., "Surgical Treatment of Wolff-Parkinson-White Syndrome: Epicardial Approach Without the Use of Cardiopulmonary Bypass," Journal of Cardiac Surgery 8: 108-116, 1993.
Surgical treatment of atrial fibrillation: a review; Europace (2004) 5, S20-S29.
Elvan et al., "Radiofrequency Catheter Ablation of the Atria Reduces Inducibility and Duration of Atrial Fibrillation in Dog," Circulation 91: 2235-2244, 1995.
Cox et al., "Modification of the Maze Procedure for Atrial Flutter and Atrial Fibrillation. I. Rational and Surgical Results," The Journal of Thoracic Cardiovascular Surgery 110: 473-484, 1995.
Cox, "The Maze III Procedure for Treatment of Atrial Fibrillation," Sabiston DC, ed Atlas of Cardiothoracic Surgery, Philadelphia: WB Saunders: 460-475, 1994.
Tsui et al., "Maze 3 for Atrial Fibrillation: Two Cuts Too Few?" PACE 17: 2163-2166, 1994.
Kosakai et al., "Cox Maze Procedure for Chronic Atrial Fibrillation Associated with Mitral Valve Disease," The Journal of Thoracic Cardiovascular Surgery 108: 1049-1055, 1994.
Cox et al., "The Surgical Treatment of Atrial Fibrillation, IV Surgical Technique," *J of Thorac Cardiovasc Surg*, 1991: 101: 584-593.
Nardella, "Radio Frequency Energy and Impedance Feedback," SPIE vol. 1068, Catheter Based Sensing and Imaging Technology (1989).
Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.
Sie et al., "Radiofrequency Ablation of Atrial Fibrillation in Patients Undergoing Mitral Valve Surgery. First Experience," Circulation (Nov. 1996) 96:450,I-675,#3946.
Sie et al., "Radiofrequency Ablation of Atrial Fibrillation in Patients Undergoing Valve Surgery," Circulation (Nov. 1997) 84:1450,#2519.
Jais et al., "Catheter Ablation for Paroxysmal Atrial Fibrillation: High Success Rates with Ablation in the Left Atrium," Circulation (Nov. 1996) 94:I-675,#3946.
Cox, "Evolving Applications of the Maze Procedure for Atrial Fibrillation," Ann Thorac Surg, 1993;55:578-580.
Cox et al. "Five-Year Experience with the Maze Procedure for Atrial Fibrillation," Ann Thorac Surg, 1993; 56:814-824.
Avitall et al., "New Monitoring Criteria for Transmural Ablation of Atrial Tissues," Circulation, 1996;94(Supp 1):I-493, #2889.
Cox et al., "An 8 1/2 Year Clinical Experience with Surgery for Atrial Fibrillation," Annals of Surgery, 1996;224(3):267-275.
Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.
Haissaguerre et al., "Right and Left Atrial Radiofrequency Catheter Therapy of Paroxysmal Atrial Fibrillation," Journal of Cardiovascular Electrophysiology, 1996;7(12):1132-1144.
Haissaguerre et al., "Role of Catheter Ablation for Atrial Fibrillation," Current Opinion in Cardiology, 1997;12:18-23.
Kawaguchi et al., "Risks and Benefits of Combined Maze Procedure for Atrial Fibrillation Associated with Organic Heart Disease," JACC, 1996;28(4):985-990.
Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Simple Left Atrial Procedure for Chronic Atrial Fibrillation Associated with Mitral Valve Disease," Ann Thorac Surg, 1996;62:1796-1800.

Sueda et al., "Efficacy of a Simple Left Atrial Procedure for Chronic Atrial Fibrillation in Mitral Valve Operations," Ann Thorac Surg, 1997;63:1070-1075.

* cited by examiner

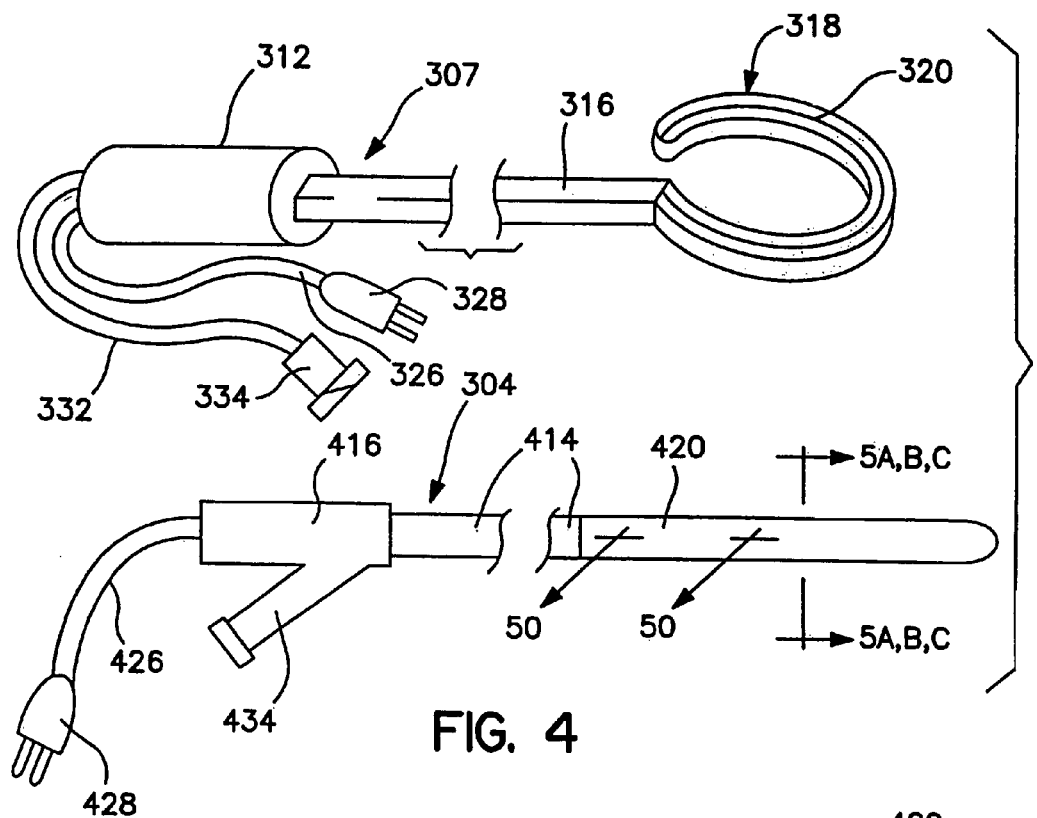
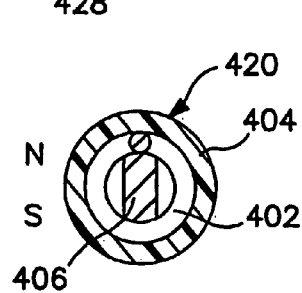
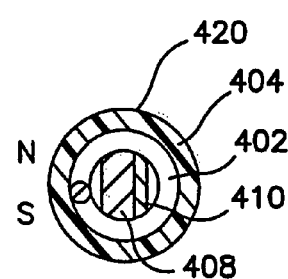
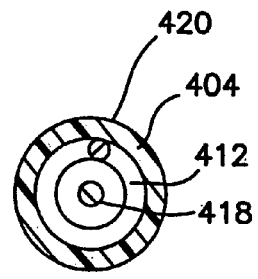
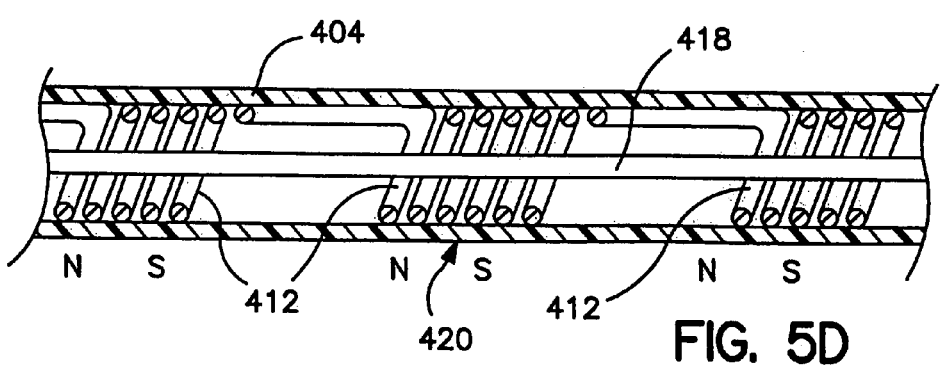
FIG. 4
FIG. 5A FIG. 5B FIG. 5C
FIG. 5D

METHOD AND APPARATUS FOR TISSUE ABLATION

CROSS-REFERENCE TO RELATED APPLICATIONS

This application is a continuation of U.S. patent application Ser. No. 11/411,261, filed Apr. 26, 2006, now U.S. Pat. No. 7,250,051, which is a continuation of U.S. patent application Ser. No. 10/756,437, filed Jan. 13, 2004, now U.S. Pat. No. 7,094,235, which is a continuation of U.S. patent application Ser. No. 10/016,297, filed Dec. 12, 2001, now U.S. Pat. No. 6,699,240, incorporated herein by reference in their respective entireties. This application also claims priority from U.S. Provisional Patent Application No. 60/286,953, filed Apr. 26, 2001, incorporated herein by reference in its entirety.

BACKGROUND OF THE INVENTION

The present invention relates to surgical tools and procedures generally and relates more particularly to the use of ablation to treat atrial fibrillation and other disorders.

In patients with chronic atrial fibrillation having tachycardia that resistant to medical treatment, the Maze procedure has been employed. This procedure controls propagation of the depolarization wavefronts in the right and left atria by means of surgical incisions through the walls of the right and left atria. The incisions create blind or dead end conduction pathways, which prevent re-entrant atrial tachycardias from occurring. While the Maze procedure is successful in treating atrial fibrillation, the procedure is quite complex and is currently practiced by only a few very skilled cardiac surgeons in conjunction with other open-heart procedures. The procedure also is quite traumatic to the heart, as in essence the right and left atria are cut into pieces and sewn back together, to define lines of lesion across which the depolarization wavefronts will not propagate.

It has been suggested that procedures similar to the Maze procedure could be instead performed by means of electrosurgical ablation, for example, by applying RF energy to internal or external surfaces of the atria to create lesions across which the depolarization wavefronts will not propagate. Such procedures are disclosed in U.S. Pat. No. 5,895,417, issued to Pomeranz, et al., U.S. Pat. No. 5,575,766, issued to Swartz, et al., U.S. Pat. No. 6,032,077, issued to Pomeranz, U.S. Pat. No. 6,142,944, issued to Swanson, et al. and U.S. Pat. No. 5,871,523, issued to Fleischman, et al, all incorporated herein by reference in their entireties. Hemostat type electrosurgical or cryo-ablation devices for use in performing such procedures are described in U.S. Pat. No. 5,733,280 issued to Avitall, U.S. Pat. No. 6,237,605 issued to Vaska, et al, U.S. Pat. No. 6,161,543, issued to Cox, et al., PCT published Application No. WO99/59486, by Wang and in pending U.S. patent application Ser. No. 09/747,609 filed Dec. 22, 2000 by Hooven, et al., all incorporated herein by reference in their entireties. In order for such procedures to be effective it is desirable that the electrosurgically created lesions are continuous along their length and extend completely through the tissue of the heart. In order for such procedures to be effective it is desirable that the electrosurgically created lesions are continuous along their length and extend completely through the tissue of the heart. Analogous issues arise when attempting to create continuous lines of lesion through the walls of other heart chambers or other organs.

SUMMARY OF THE INVENTION

According to the present invention elongated lesions as might be desired in a maze type procedure or other procedure may be produced using a set of two elongated ablation components carrying means (e.g. an electrode or electrodes) for applying ablation energy (e.g. RF energy) along its length. The ablation components are adapted to be arranged on opposite sides of the walls of the atria or other hollow organs, on either side of the organ walls and to ablate or create lesions in the tissue between the components. The ablation components may also be arranged along opposing external surfaces of an organ, for example opposite sides of an atrial appendage or along opposite sides of the tissue adjacent the bases of the right or left pulmonary veins.

The ablation components are provided with a magnetic system for drawing the components toward one another to compress the wall or walls of an atrium or other hollow organ therebetween, along the length of the components. In these systems, at least one of the components is provided with a magnet or series of magnets extending along the component. The other component is provided with a ferromagnetic member or preferably another magnet or series of magnets extending along its length, having polarity chosen to assure attraction between the two components. The magnet or magnets may be rigid or flexible and may be formed of magnetic material, e.g. rare earth magnets, or may alternatively be electromagnets.

In one preferred embodiment of the invention, the two components comprise opposing jaws of an electrosurgical hemostat, provided with elongated RF electrodes and having straight or curved configurations. In some of these embodiments, the jaws of the hemostat are both rigid and the magnets are present primarily to assure good contact and alignment between the jaws, along their length. In other embodiments, one jaw may be rigid and the other flexible, for example to allow it to be temporarily deformed to access desired locations. In these embodiments, magnetic system also assists the flexible jaw in returning to a configuration corresponding to the rigid jaw, as the jaws are brought into proximity to one another. In some embodiments, one jaw may be shapeable, so that the physician can select a desired configuration, with the other jaw being flexible. In these embodiments, the magnetic system allows the flexible jaw to automatically assume a configuration corresponding to the shapeable jaw. In other embodiments, both jaws might be flexible.

Similar sets of embodiments may be provided wherein the two components are separate from one another, for example mounted to separate handles. Alternatively, a first, external component might be mounted to a handle, to be held by the physician, while a second, internal component may be located on a percutaneously introduced catheter. In these embodiments, the internal component would typically be quite flexible, while the external component would be either rigid or shapeable. In these embodiments the magnetic system allows the internal component to automatically assume a configuration corresponding to the external component, after introduction of the internal component to the interior of the hollow organ.

BRIEF DESCRIPTION OF THE DRAWINGS

FIG. 4 is an illustration of a system employing the invention, including a first external component and a separate second internal component.

FIGS. 5A through 5D illustrate alternative embodiments of the distal portion of the internal component illustrated in FIG. 4, in cross section and longitudinal section.

DESCRIPTION OF THE PREFERRED EMBODIMENTS

Figure 1:
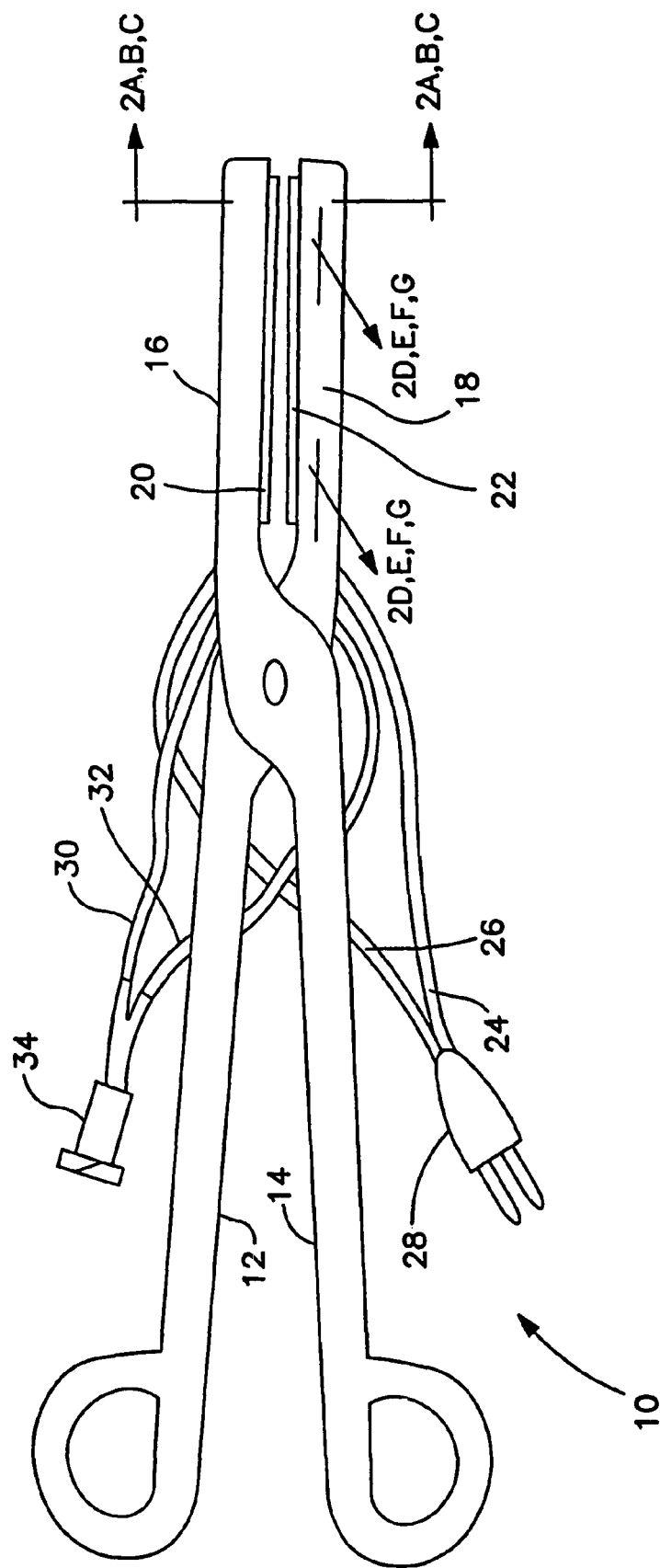
FIG. 1 is a plan view of hemostat of the type in which the present invention may be embodied.

FIG. 1 is a plan view illustrating a bipolar electrosurgical hemostat of a type in which the present invention may usefully be practiced. The hemostat is provided with handles 14 and 12, coupled to pivoting jaws 16 and 18, respectively. Located along jaws 16 an 18 are ablation electrodes 20 and 22, which, as discussed below, take the form of RF electrodes. In alternative embodiments, electrodes 20 and 22 may be employed to apply microwave radiation, or might be replaced by elongated heating or cooling elements to provide for thermal or cryo-ablation along their length. In the embodiment illustrated, the electrodes are irrigated RF electrodes, allowing for delivery of saline or other conductive fluid along their lengths, generally according to the mechanism as described in U.S. Pat. No. 6,096,037 issued to Mulier, incorporated herein by reference in its entirety. Each electrode is provided with a fluid delivery lumen 30, 32, through which the saline or other conductive fluid is delivered to the electrodes. Lumens 30 and 32 are coupled to a luer fitting 34, which may be coupled to a source of conductive fluid. Separate luer fittings for each of lumens 30, 32 might alternatively be provided. Similarly, each electrode is provided with conductors 24, 26 allowing the electrodes to be coupled to a source of ablation energy via electrical connector 28, as noted above. The source of ablation energy may provide RF energy or microwave energy. In alternative embodiments in which electrodes 20 and 22 are replaced by heaters, the fluid delivery lumens may not be provided, and instead, electrical conductors 24 and 26 may be coupled to two elongated resistive heaters arranged along jaws 16 and 18, and coupled to an electrical power source via connector 28. In alternative embodiments in which elongated cooling elements are substituted for electrodes 20 and 22, cooling fluid might be delivered to electrodes via fluid lumens 30 and 32 or alternatively, in the event electrical cooling devices are provided, electrical power might be delivered to the cooling devices via connectors 24 and 26 through electrical connector 28.

While the discussion below focuses on ablation systems in which the particular ablation energy delivered is RF energy, delivered via irrigated electrodes, it should be understood that the present invention can usefully be practiced in conjunction with the other forms of ablation energy referred to above. As such, for purposes of the following discussion, the illustrated and described irrigated RF electrodes should be taken as exemplary of a mechanism for applying ablation energy according to the present invention, rather than as limiting.

Jaws 16 and 18 may have a straight configuration as illustrated, or may be curved. Jaws 16 and 18 are preferably manufactured of a non-ferromagnetic material such a biocompatible plastic, and, as discussed below, carry an elongated magnet or series of magnets, extending along the electrodes 20 and 22, in order to assist in aligning the electrodes relative to one another on opposite sides of tissue to be ablated and to assist in compressing tissue between the electrodes to assure good contact along their length. As described in more detail, jaws 16 and 18 may be rigid, shapeable, or flexible, depending on the particular embodiment of the invention being practiced.

Figure 2A:
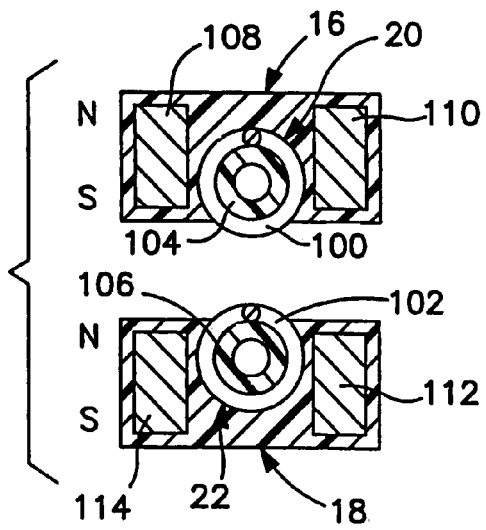
FIGS. 2A through 2G illustrate alternative configurations for the jaws of the hemostat of FIG. 1, illustrating alternative embodiments of the present invention in cross section and longitudinal section.

FIGS. 2A through 2G illustrate various alternative embodiments of the invention, employing different types of magnetic alignment systems and different configurations for the first and second components (in this case the jaws 16 and 18), along which ablation energy is to be applied. FIG. 2A illustrates a cross sectional view through jaws 16 and 18 of the hemostat of FIG. 1, in which the electrodes 20 and 22 take the form of elongated electrode coils 100, 102, respectively, carrying internal porous tubes 104 and 106. Tubes 104 and 106 may be fabricated, for example, of porous polytetrafluoroethylene (PTFE), and have their internal lumens coupled to the fluid lumens 30 and 32 illustrated in FIG. 1. By this mechanism, delivery of conductive fluid such as saline solution along the length of the electrode coils 101 and 102 may be accomplished. While as described, the electrodes 20 and 22 each include a single elongated electrode coil embodiments in which the components (jaws 16 and 18) are provided with multiple electrodes arranged along their length are also within the scope of the present invention.

As illustrated, jaws 16 and 18 are each provided with a pair of magnets or a series of magnets 108, 110, 112, 114, which extend along the jaws 16 and 18. These magnets, shown in cross section, may either be individual elongated magnets or may be a series of shorter magnets, extending along the jaws. The polarities of magnets correspond to the "N" and "S" markings as illustrated, arranged such that the jaws 16 and 18 are attracted to one another along their lengths. Provision of magnets on both sides of the electrodes 18 and 20 assist in assuring that the electrodes will center themselves with respect to one another so that the electrodes will be located directly across from one another when placed on opposite sides of tissue to be ablated. The magnets also assist in compressing the jaws of the hemostat along their length, assuring good contact with the tissue along the length of the jaws.

Jaws 16 and 18 are preferably fabricated of a non-ferromagnetic material, such as a plastic, so that the magnets and electrode coils as illustrated may be insulated from one another. In some embodiments, both jaws 16 and 18 may be rigid and may be pre-formed with the same configuration so that they are parallel to one another. Alternatively, one of jaws 16 and 18 may be rigid, while the other of the two jaws may be quite pliant or flexible, so that upon placement of the jaws on either side of the wall of a hollow organ to be ablated, the magnetic force provided by the magnets causes the flexible jaw to assume a configuration parallel to the rigid jaw and to compress the wall of the hollow organ between the jaws. In additional alternative embodiments, one of the two jaws 16 and 18 may be shapeable by the physician, to assume a desired configuration, with the other of the two jaws being flexible. In this embodiment as well, the flexible jaw is aligned and configured parallel to the shapeable jaw when the two jaws are brought towards one another on either side of the wall of the hollow organ to be ablated. The shapeable jaw may be shapeable by virtue of the material chosen to fabricate the jaw, or means of a shapeable insert, for example, a longitudinally extending rod of nitinol, stainless steel, or other shapeable metal, not illustrated in FIG. 2A.

Figure 2B:
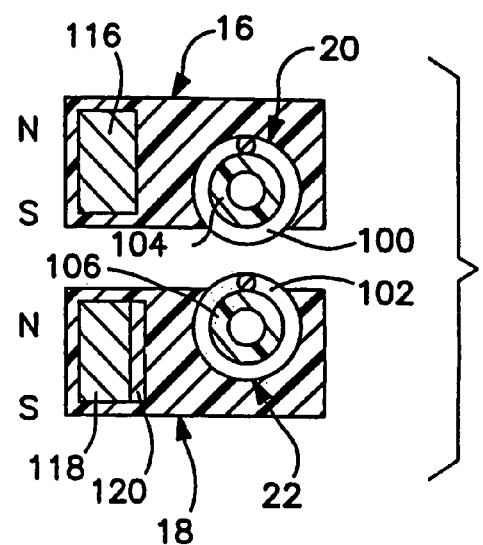

FIG. 2B illustrates an alternative embodiment of an invention according to the present invention, similarly showing a cross section through jaws 16 and 18 of the hemostat of FIG. 1. All elements correspond to identically numbered elements in FIG. 2A. In this embodiment, only a single elongated electrode or line of electrodes 116, 118 is provided for each of the two jaws 16, 18 respectively. This configuration allows for a reduction in the overall size of the jaws, but otherwise functions as described in conjunction with FIG. 2A. In FIG. 2B, an optional metallic shaping wire 120 is shown, mounted adjacent to the magnet or magnets 118, to allow the physician to shape jaw 18. In embodiments in which this shaping wire is present, it is to be expected that jaw 16 would be flexible, and would conform to the configuration provided to jaw 18 by the physician, after placement of the jaws on opposite sides of tissue to be ablated.

Figure 2C:
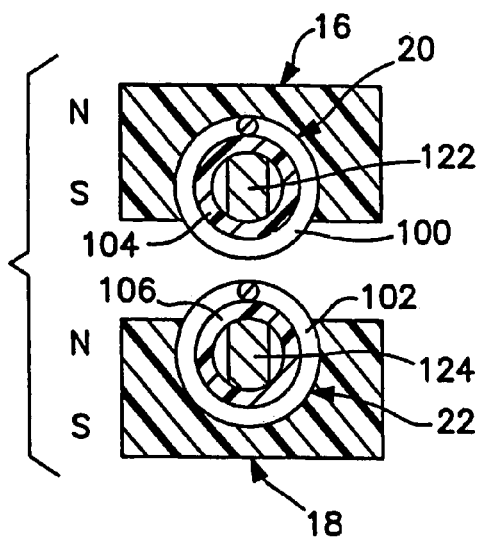

FIG. 2C illustrates a third alternative embodiment of the present invention, also taking the form of a cross section through jaws 16 and 18 of the hemostat of FIG. 1. Identically, numbered components correspond to those illustrated in FIG. 2A. In this embodiment, elongated magnets or series of magnets 122 and 124 are located within the porous fluid lumens 106 and 104, so that magnetic force applied to draw the jaws 16 and 18 toward one another is applied centered with respect to the electrode coils 100 and 102. The various alternative embodiments discussed above in conjunction with FIGS. 2A and 2B may correspondingly be provided in conjunction with the jaws having the general configuration illustrated in FIG. 2C.

As illustrated in 2A, 2B and 2C, the magnets are arranged so that the south pole(s) of the magnet(s) of one jaw are adjacent to the north pole(s) of the magnet(s) of the other jaw. This configuration will be most desirable in conjunction with embodiments in which single, elongated magnets extend essentially along the length of the jaws, and also in embodiments in which a series of shorter, closely spaced magnets extending along the jaws is provided. In embodiments in which magnets extend along the jaw but are more substantially spaced from one another, the polarity of the magnets may be altered, so that along one jaw, the north poles of the magnets may be located at the distal ends of the magnets and the south poles located at the proximal ends wherein on the other jaw, the south poles of the magnets will be located at their distal ends and north poles of the magnets will be located at proximal ends. Alternative magnetic configurations such as this may be employed in any of the embodiments illustrated in FIGS. 2A, 2B and 2C in which the magnets take the form of series of spaced, magnets, running along the lengths of the jaws.

The magnets themselves may be of any appropriate magnetic material. One particularly desirable set of magnetic materials for use in the present invention may be rare earth magnets, due to their extraordinary strength for relatively small sizes and weights. However, elongated flexible magnets might be substituted, as well as ceramic magnets. In addition, as discussed in more detail below, the magnets may be replaced with electromagnetic coils. In further alternative embodiments, it may be possible to employ magnets located in only one of the jaws, substituting a ferromagnetic material such as magnetic stainless steel for the other of the two magnets. For example, in the embodiment illustrated in FIG. 2A, magnets 108 and 110 might be replaced be elongated magnetic stainless steel members. In such an embodiment, the elongated stainless steel members would be attracted to the magnets 112 and 114 as described below and might also be employed to provide the ability to shape the jaw 116 to a desired configuration. Similar substitutions of non-magnetized ferromagnetic materials for the magnets illustrated in FIGS. 2B and 2C are also believed within the scope of the present invention.

Figure 2D:
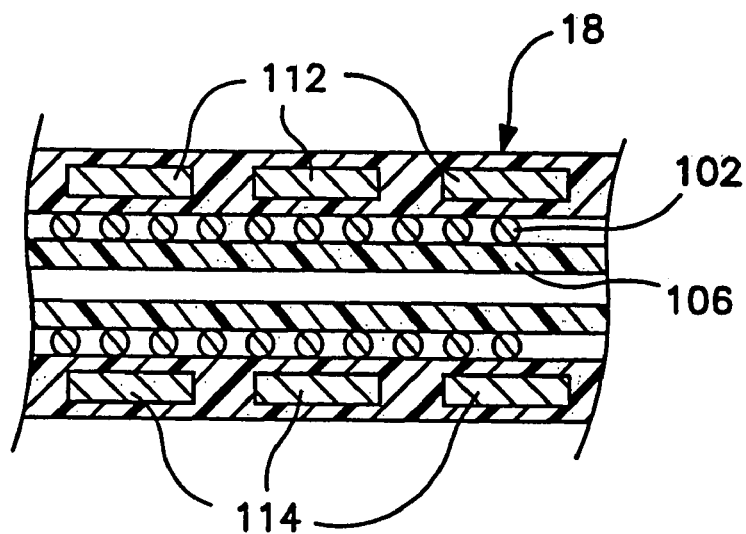

FIG. 2D is a longitudinal sectional view through jaw 18 of the hemostat of FIG. 1. In this embodiment, the magnets 112 and 114 take the form of a series of magnets, mounted within the body of jaw 18. Electrode coil 102 and fluid lumen 106 are also illustrated in longitudinal section.

Figure 2E:
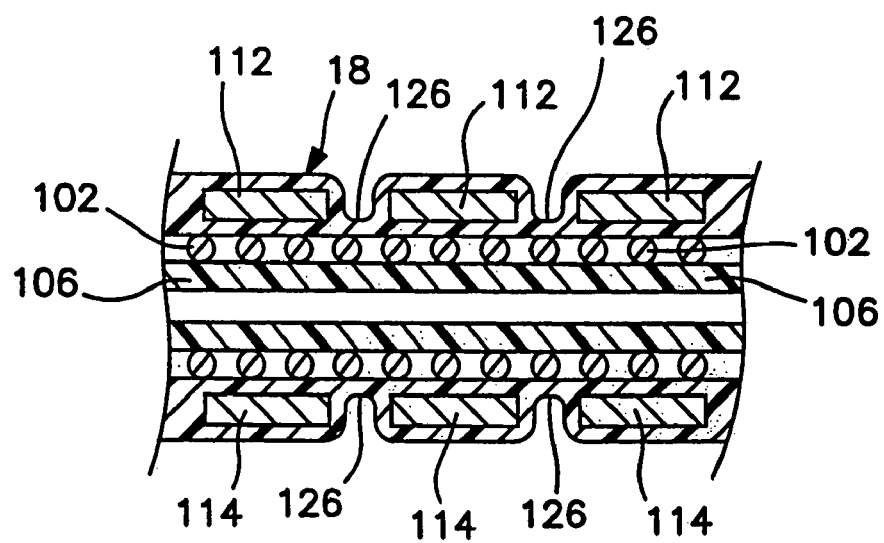

FIG. 2E illustrates an alternative longitudinal sectional view through jaw 18, otherwise as illustrated in FIGS. 1 and 2A. Components corresponds to identically numbered components in FIG. 2A. In this embodiment, however, jaw 18 is provided with indentations 126 in between the individual magnets 114 and 112. These indentations, in conjunction with fabrication of the jaw 18 of the flexible material, define hinge points, facilitating bending of the jaw 18. Such a configuration will be particularly desirable in the event that jaw 16 as illustrated in FIGS. 1 and 2A were to be made rigid or shapeable, with jaw 18 being flexible enough to adapt to the configuration of jaw 16, when placed on the opposite side of tissue to be ablated.

Figure 2F:
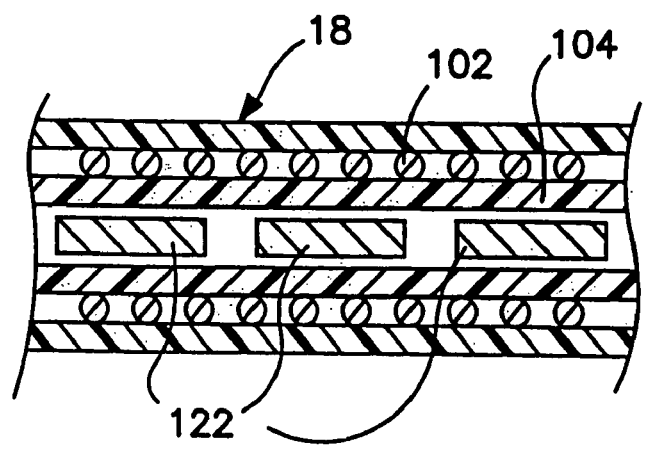

FIG. 2F is a longitudinal sectional view through a hemostat having a jaw configuration as illustrated in FIG. 2C. Components correspond to identically numbered components in FIG. 2C. In this view, the magnet 122 takes the form of a series of magnets located within fluid lumen 104.

Figure 2G:
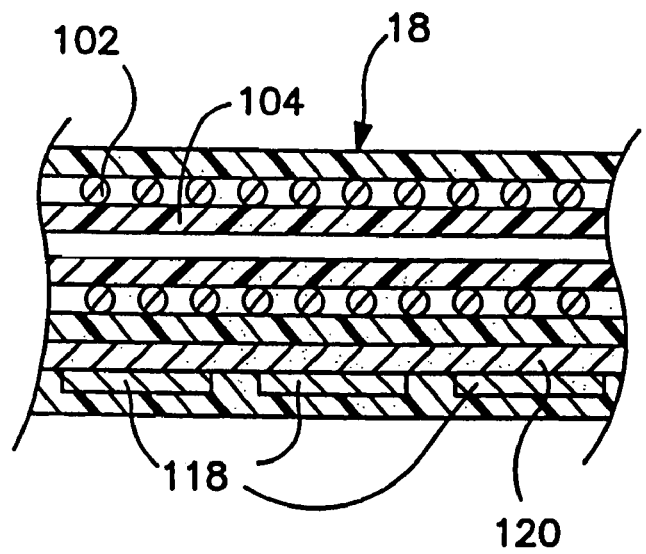

FIG. 2G illustrates a longitudinal section through an embodiment of the present invention having a jaw configuration as illustrated in FIG. 2B. In this embodiment, the magnet 118 take the form a series of magnets 118, located along side the shaping wire 120. Electrode coil 102 and fluid lumen 104 are also visible.

In the embodiments of FIGS. 2D, 2F and 2G, it should be understood that elongated continuous magnets, flexible or rigid might be substituted for a series of individual magnets as illustrated. In addition, it should also be understood that in some embodiments, the magnets as illustrated might be more widely spaced from another, and arranged so that their north/south magnetic access extends longitudinally along the lengths of the jaws, as described above in conjunction with FIGS. 2A through 2C. In such embodiments, the north/south magnetic axes of the magnets in one jaw would be opposite those of the magnets in the other jaw. Jaws employing this arrangement of magnets might also be used in conjunction with a jaw or other ablation component taking the form of a series of electro magnets, for example, coils having their axes extending along the axes of the jaws or other ablation components.

Figure 3:
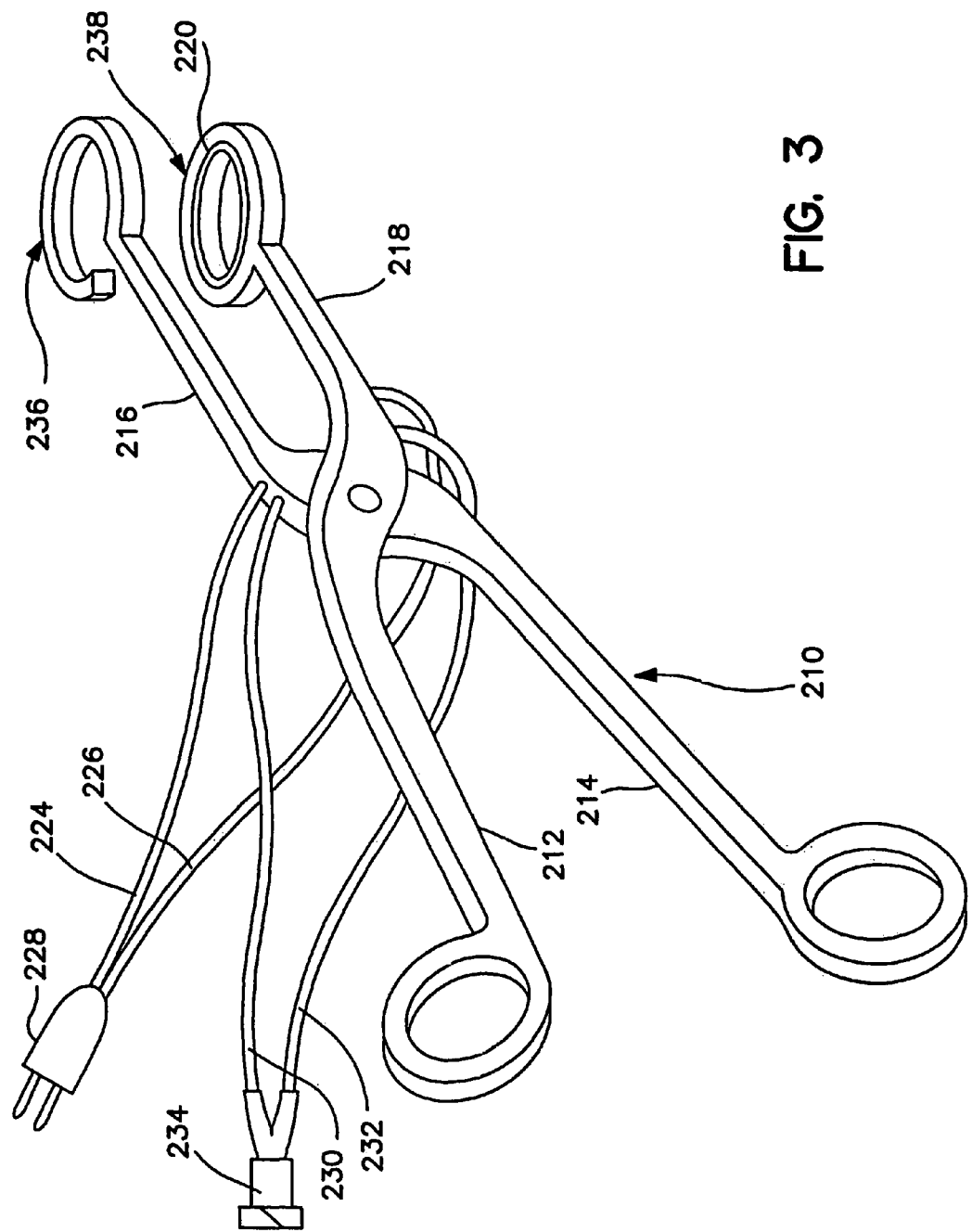
FIG. 3 is a perspective view of a hemostat of a second type, in which the present invention may be usefully practiced.

FIG. 3 is a perspective view of a bipolar electrosurgical hemostat of a second type, appropriate for use in conjunction with the present invention. In this embodiment the hemostat is provided with handles 212 and 214 and elongated jaws 216 and 218. In this case, jaw 218 carries a circular ablation component 238, along which an electrode 220 is arranged. Jaw 216 is provided with a hook shaped ablation component 236, carrying a corresponding electrode facing electrode 220. The instrument of FIG. 3 is particularly adapted for ablations and circling the bases of the pulmonary veins, in the context of an electrosurgical procedure analogous to a maze procedure as discussed above. In this embodiment, it may be desirable that the circular ablation component 238 is either rigid or shapeable by the physician, to allow adaptation of the configuration of the component to this particular anatomy of the patient involved. Component 236 is preferably at least flexible enough to be spread open slightly to facilitate placing of the jaw around the basis of the pulmonary veins and may be quite flexible, relying on the magnetic attraction between components 236 and 238 and to cause component 236 to assume a configuration parallel to component 238. As in conjunction with the hemostat illustrated in FIG. 1, fluid lumens 230 and 232 are provided to allow delivery of a conductive fluid to the electrodes, via luer fitting 234. Electrical conductors 224 and 226 are provided to conduct electrical energy to the electrodes, via electrical connector 228. As discussed above in conjunction with the hemostat of FIG. 1, alternative means for applying ablation energy such as microwave antenna or heaters or coolers to provide thermal or cryo-ablation may be substituted for the electrodes.

FIG. 4 illustrates an additional alternative embodiment of the invention, in which the two ablation components are separate from one another rather than being joined as in the hemostats of FIGS. 1A and 3. In this embodiment, the first component corresponds generally to jaw 216 of the hemostat of FIG. 3, provided in this case with a handle 312 allowing the physician to manipulate the device. An electrode 320 extends around the curved ablation component 318, and may be, as discussed above, an irrigated electrosurgical electrode, provided with fluid via lumen 332 and luer fitting 334 and provided with electrical power via conductors 326 and electrical connector 328. In use, the curved ablation component 318 will be placed on the exterior surface of the organ to be ablated, for example, placed around the bases of a patient's pulmonary veins. In this particular embodiment, the curved ablation component 318 is preferably rigid or malleable, as the internal ablation component 304, as discussed below, will be quite flexible.

The internal ablation component 304 takes the form of a catheter having an elongated catheter body 414 carrying an electrode along its distal portion 420. Distal portion 420 may have a structure corresponding generally to the illustrated structures for the jaws of the hemostats as illustrated in FIGS. 2A through 2G, with the caveat that the structure of a distal portion 420 of the catheter should be fabricated of a sufficiently flexible material that it may be introduced percutaneously and navigated to the desired location within the organ to be ablated. For example, the catheter might be advanced through the vascular system to the interior of the left atrium, to a position adjacent the openings into the pulmonary veins. Alternatively, as illustrated in FIGS. 5A through D below, the distal portion 420 of the catheter may be specifically optimized for location at the distal portion of a catheter. As illustrated, the proximal end of the catheter is provided with a fitting 416 carrying a fluid coupling 434 allowing delivery of saline or other conductive fluid to the electrode located along the distal portion 420 of the catheter. Electrical power is provided to the electrode by means of conductors 426 and connector 428 in a fashion analogous to that described above for the other embodiments.

FIGS. 5A-5D illustrate various alternative configurations for the distal portion 420 of the catheter 304 illustrated in FIG. 4. The embodiments of the invention as illustrated in FIGS. 5A-5D may also be employed in external ablation components as illustrated in FIG. 4 or in hemostat type devices as illustrated in FIGS. 1 and 3.

FIG. 5A is cross sectional view through the distal portion 420 of the catheter illustrated in FIG. 4, showing a first embodiment of invention particularly optimized for use as part of a percutaneously introduced catheter. In this embodiment, the outer surface of the distal portion comprises a porous tube 404, which may be made of PTFE as discussed above, surrounding an electrode coil 402. A magnet or series of magnets 406 is mounted within the lumen of the electrode coil 402. In this embodiment, fluid is delivered through the lumen of the electrode coil 402, permeates through the porous wall of tube 404, and electrical energy provided by electrode 402 is coupled to the tissue to be ablated via the conductive fluid in the wall and on the surface of tube 404. As illustrated, the electrode is shown having its magnetic polarity such that its north/south axis runs transverse to the axis of the catheter. However, alternative embodiments employing a series of spaced magnets having their north/south axis running along the axis of the catheter are also within the scope of the invention.

FIG. 5B shows an alternative cross section through the distal portion 420 of the catheter FIG. 4. Numbered elements correspond to identically numbered elements in FIG. 5A. In this embodiment, however, a shaping wire 410 is shown, allowing the physician to provide a desired configuration to the distal portion 420 of the catheter. For example, the catheter may be biased to assume a generally circular configuration, which is straightened during the passage of the catheter through the vascular system, with shaping wire 410 allowing it to resume its desired configuration when no longer retrained by vascular system.

FIG. 5C shows an additional alternative cross section through the distal portion 420 of the catheter FIG. 4. Numbered elements correspond to identically numbered elements in FIG. 5A. In this embodiment, coil 412, however is not an ablation electrode but instead is employed as an electromagnet to attract the catheter to an associated external ablation component. Delivery of ablation energy, e.g. RF or microwave, is accomplished by central wire 418.

FIG. 5D shows a longitudinal sectional view through the distal portion 420 of a catheter having a cross section as illustrated in FIG. 5C. Numbered elements correspond to identically numbered elements in FIG. 5C. In this view it can be seen that coil 412 is one of a series of spaced electromagnet coils spaced along the distal portion 420 of the catheter. As illustrated, coils 412 are wired in series, however, in alternative embodiments they may be wired for individual activation.

In conjunction with the above disclosure, I claim:

1. A tissue ablation device comprising: a first component comprising a first magnetically attractive element, a portion of the first component being manually shapeable, wherein the first component is a first ablation component comprising a cryo-ablation component for delivery of cryo-ablation energy; and,
   a second component comprising a second magnetically attractive element for magnetically attracting the first and second components toward one another, the second component additionally being mechanically coupled to the first component; a portion of the second component being sufficiently flexible to be deflected into alignment with the first component by the magnetically attractive elements.

2. A system as in claim 1 wherein the second component is a second ablation component for delivery of an ablation energy.

3. A system as in claim 1 wherein at least one of the magnetically attractive elements comprises a rare earth magnet.

4. A system as in claim 1 wherein at least one of the magnetically attractive elements comprises an electromagnet.

5. A system as in claim 1 wherein the first and second components are pivotally coupled to one another.

6. A system as in claim 1 wherein the first and second components comprise jaws of a hemostat.

* * * * *